United States Patent
Liu et al.

(10) Patent No.: US 10,054,527 B2
(45) Date of Patent: Aug. 21, 2018

(54) METHOD AND SYSTEM FOR BENDING TEST OF FLEXIBLE SCREEN

(71) Applicants: Kunshan New Flat Panel Display Technology Center Co., Ltd., Kunshan, Jiangsu (CN); Kunshan Go-Visionox Opto-Electronics Co., Ltd., Kunshan, Jiangsu (CN)

(72) Inventors: Dongdong Liu, Jiangsu (CN); Sheng Gao, Jiangsu (CN); Xiuqi Huang, Jiangsu (CN)

(73) Assignees: KUNSHAN NEW FLAT PANEL DISPLAY TECHNOLOGY CENTER CO., LTD., Kunshan (CN); KUNSHAN GO-VISIONOX OPTO-ELECTRONICS CO., LTD., Kunshan (CN)

( * ) Notice: Subject to any disclaimer, the term of this patent is extended or adjusted under 35 U.S.C. 154(b) by 0 days.

(21) Appl. No.: 15/105,963

(22) PCT Filed: Dec. 17, 2014

(86) PCT No.: PCT/CN2014/094112
§ 371 (c)(1),
(2) Date: Jun. 17, 2016

(87) PCT Pub. No.: WO2015/090207
PCT Pub. Date: Jun. 25, 2015

(65) Prior Publication Data
US 2017/0102301 A1    Apr. 13, 2017

(30) Foreign Application Priority Data
Dec. 18, 2013  (CN) .......................... 2013 1 0698549

(51) Int. Cl.
*G01N 3/20* (2006.01)
*G01M 99/00* (2011.01)
(Continued)

(52) U.S. Cl.
CPC ............ *G01N 3/20* (2013.01); *G01M 99/007* (2013.01); *G01N 3/08* (2013.01); *G01N 19/08* (2013.01);
(Continued)

(58) Field of Classification Search
CPC ... G01N 2203/0282; G01N 2203/0023; G01N 2203/0067; G01N 2203/0005;
(Continued)

(56) References Cited

U.S. PATENT DOCUMENTS 5,616,848 A * 4/1997 Hemingway ............ G01N 3/20
73/838
6,776,050 B2  8/2004 Auch et al.
(Continued)

FOREIGN PATENT DOCUMENTS

CN   2837820 Y   11/2006
CN   200975965 Y  11/2007
(Continued)

OTHER PUBLICATIONS

International Search Report for International Application No. PCT/CN2014/094112 dated Mar. 24, 2015.
(Continued)

*Primary Examiner* — Jonathan Dunlap
(74) *Attorney, Agent, or Firm* — Finnegan, Henderson, Farabow, Garrett & Dunner, LLP

(57) ABSTRACT

A method for bending test of a flexible screen is disclosed, including: connecting the flexible screen to a fixing device to form two connection ends; and conducting an extrusion test to the flexible screen, including moving the fixing device
(Continued)

to change the distance between the connection ends of the fixing device so that the distance is less than or equal to the length of the flexible screen between the two connection ends. A system for bending test of a flexible screen is also disclosed. The above method and system for bending test of a flexible screen, which can simulate an operational environment of the flexible screen by moving the fixing device to conduct an extrusion test to the flexible screen, can reduce testing costs compared with the traditional methods and apparatuses for bending test of a flexible screen.

5 Claims, 4 Drawing Sheets

(51) Int. Cl.
  *G01N 19/08* (2006.01)
  *G01N 3/08* (2006.01)
(52) U.S. Cl.
  CPC ........... *G01N 2203/0003* (2013.01); *G01N 2203/0005* (2013.01); *G01N 2203/0023* (2013.01); *G01N 2203/0037* (2013.01); *G01N 2203/0067* (2013.01); *G01N 2203/0278* (2013.01); *G01N 2203/0282* (2013.01); *G01N 2203/0641* (2013.01)
(58) Field of Classification Search
  CPC ... G01N 2203/0003; G01N 2203/0037; G01N 2203/0278; G01N 2203/0641; G01N 3/20; G01N 19/08
  USPC .................. 73/849–854, 760, 812
  See application file for complete search history.

(56) References Cited

U.S. PATENT DOCUMENTS

| | | | |
|---|---|---|---|
| 7,181,979 B1 | 2/2007 | Lin et al. | |
| 8,461,860 B2* | 6/2013 | Kim .................. | G01M 5/005 324/762.01 |
| 8,943,898 B2* | 2/2015 | Bell .................. | G02F 1/1309 73/856 |
| 2003/0061885 A1 | 4/2003 | Auch et al. | |
| 2006/0137465 A1* | 6/2006 | Lee .................. | G01N 3/20 73/794 |
| 2007/0193364 A1* | 8/2007 | Wong .................. | G01N 3/20 73/849 |
| 2008/0083288 A1* | 4/2008 | Glaesemann ........... | G01N 3/20 73/849 |
| 2008/0229844 A1* | 9/2008 | Mackey .............. | G01M 5/0033 73/852 |
| 2009/0272198 A1* | 11/2009 | Wen .................. | G01N 3/20 73/849 |
| 2011/0248739 A1 | 10/2011 | Kim et al. | |
| 2012/0067134 A1* | 3/2012 | Bell .................. | G02F 1/133305 73/800 |
| 2012/0285257 A1 | 11/2012 | Kim | |
| 2013/0327152 A1* | 12/2013 | Chen .................. | G01N 3/08 73/818 |
| 2014/0174195 A1* | 6/2014 | Shen .................. | G01N 3/20 73/851 |
| 2014/0238145 A1* | 8/2014 | Tran .................. | G01N 3/20 73/851 |
| 2014/0333333 A1 | 11/2014 | Seol et al. | |
| 2015/0033870 A1* | 2/2015 | Lee .................. | G01N 3/20 73/849 |
| 2016/0103048 A1* | 4/2016 | Okazaki .............. | G01N 3/20 73/853 |

FOREIGN PATENT DOCUMENTS

| | | |
|---|---|---|
| CN | 101295219 A | 10/2008 |
| CN | 101581573 A | 11/2009 |
| CN | 101726442 A | 6/2010 |
| CN | 202383033 U | 8/2012 |
| CN | 102809513 A | 12/2012 |
| CN | 102818732 A | 12/2012 |
| CN | 102980815 A | 3/2013 |
| CN | 103149044 A | 6/2013 |
| JP | S 62-44239 U | 3/1987 |
| JP | H03200047 A | 9/1991 |
| JP | H09281023 A | 10/1997 |
| JP | H1172422 A | 3/1999 |
| JP | 2004279083 A | 10/2004 |
| JP | 2005315691 A | 11/2005 |
| JP | 2013148577 A | 8/2013 |
| KR | 10-2006-0089295 A | 8/2006 |
| KR | 10-2012-0034885 A | 4/2012 |
| KR | 20120127037 A | 11/2012 |
| TW | 200916748 A | 4/2009 |
| TW | 201319516 A | 5/2013 |

OTHER PUBLICATIONS

Written Opinion for International Application No. PCT/CN2014/094112 dated Mar. 12, 2015.
First Office Action for Chinese Patent Application No. 201310698549.8, dated Nov. 15, 2016.
Search Report for First Office Action for Chinese Patent Application No. 201310698549.8, dated Nov. 15, 2016.
Second Office Action for Chinese Patent Application No. 201310698549.8, dated Jun. 9, 2017.
Supplementary Search Report for Second Office Action for Chinese Patent Application No. 201310698549.8, dated Jun. 9, 2017.
Office Action for Taiwan Patent Application No. 103144247, dated Feb. 15, 2017.
Notification of Grounds for Rejection for Japanese Patent Application No. 2016-541044, dated Jul. 14, 2017.
Extended European Search Report and Written Opinion for European Patent Application No. 14870875.3, dated Jul. 13, 2017.
Office Action for Korean Patent Application No. 10-2016-7019017, from the Korean Intellectual Property Office, dated Apr. 18, 2017.

\* cited by examiner

METHOD AND SYSTEM FOR BENDING TEST OF FLEXIBLE SCREEN

CROSS-REFERENCE TO RELATED APPLICATIONS

This application is a national phase application based on PCT/CN2014/094112, filed Dec. 17, 2014, which claims the priority of Chinese Patent Application No. 201310698549.8, filed Dec. 18, 2013, the contents of both of which are incorporated herein by reference.

FIELD

The present disclosure relates generally to the technical filed of flexible device test, and more particularly, to a method and a system for bending test of a flexible screen.

BACKGROUND

A flexible display is a deformable and flexible display unit, made of a soft material. The flexible display can be as thin as paper, and even if the power is cut off, the content in the display will not disappear, so the flexible display is also referred to as "electronic paper". Because of the characteristics of being extremely light and thin and having low power consumption and being deformable, the flexible display is already widely used in portable electronic devices. The bending performance of the flexible screen of the flexible display directly affects the quality of the flexible display, so it is necessary to make an evaluation on the bending performance of the flexible screen, that is, detect the bending performance of the flexible screen after conducting an extrusion bending test to the flexible screen.

A drum-type bending device is always used in traditional methods and devices for bending test of flexible screen to mechanically bend the flexible screen. Specifically, a number of drums of a same curvature or different curvatures can be used to transmit the flexible screen to bend the flexible screen. If only one drum is used to transmit the flexible screen, a relative unit is required to press the flexible screen to bend the flexible screen; and if a plurality of drums are used to transmit the flexible screen, a drawing device is required to draw the flexible screen so that the flexible screen can be normally transmitted on the plurality of drums. Using a drum or a plurality of drums to transmit and bend the flexible screen has disadvantages of complexity of operation and high-cost of testing.

SUMMARY

In view of the above, there is a need to provide to a method and a system for bending test of a flexible screen, which is low cost.

According to an aspect of the present disclosure, a method for bending test of a flexible screen is provided, including:
  connecting the flexible screen to a fixing device to form two connection ends; and
  conducting an extrusion test to the flexible screen, including moving the fixing device to change the distance between the connection ends of the fixing device so that the distance is less than or equal to the length of the flexible screen between the two connection ends.

In one embodiment, conducting an extrusion test to the flexible screen includes:
  extruding the flexible screen in a direction along a connecting line between the two connection ends; or
  moving the fixing device respectively along directions which are parallel to each other to extrude the flexible screen.

In one embodiment, extruding the flexible screen in the direction along the connecting line between the two connection ends includes: moving the fixing device in a direction along the connecting line between the two connection ends for a predetermined magnitude, in which a plurality of predetermined magnitudes are provided, and extruding the flexible screen at a predetermined number of times.

In one embodiment, moving the fixing device respectively along directions which are parallel to each other to extrude the flexible screen includes:
  moving the fixing device respectively along a first plurality of directions which are parallel to each other to extrude the flexible screen, and moving the fixing device respectively along a second plurality of directions which are parallel to each other to extrude the flexible screen, in which the first plurality of directions is perpendicular to the second plurality of directions.

In one embodiment, conducting an extrusion test to the flexible screen includes moving the fixing device in the first plurality of directions for a preset magnitude to extrude the flexible screen at a first preset number of times, and moving the fixing device in the second plurality of directions for a predetermined magnitude to extrude the flexible screen at a second preset number of times.

In one embodiment, there are a plurality of preset magnitudes and/or a plurality of predetermined magnitudes.

In one embodiment, the two connection ends are located on opposite sides of the flexible screen respectively, and the connecting line between the two connection ends is perpendicular to a side edge of the flexible screen.

According to another aspect of the present disclosure, a system for bending test of a flexible screen is provided, including:
  a fixing device, configured to be connected to the flexible screen to form two connection ends; and
  an extrusion device, configured to move the fixing device to change the distance between the connection ends of the fixing device so that the distance is less than or equal to the length of the flexible screen between the two connection ends, for conducting an extrusion test to the flexible screen.

In one embodiment, the fixing device includes a first clamp and a second clamp configured to be connected to opposing sides of the flexible screen respectively to form two connection ends.

In one embodiment, the extrusion device includes:
  a fixing support;
  a stretchable first tension rod and a stretchable second tension rod, one end of the first tension rod and one end of the second tension rod being connected to the first clamp and the second clamp respectively,
  a first base and a second base, provided on the fixing support, and configured to be moveable relative to the fixing support and connected to the other end of the first tension rod and the other end of the second tension rod respectively, and to control the length of each of the first tension rod and the second tension rod to be stretched, to extrude the flexible screen in the direction along the connecting line between the two connection ends or move the fixing device respectively along directions which are parallel to each other to extrude the flexible screen.

In one embodiment, the first clamp and the second clamp are movably connected with the first tension rod and the second tension rod respectively.

The above method and system for bending test of a flexible screen connect the flexible screen to a fixing device to form two connection ends, and move the fixing device to change the distance between the connection ends of the fixing device so that the distance is less than or equal to the length of the flexible screen between the two connection ends for conducting an extrusion test to the flexible screen. The above method and system for bending test of a flexible screen according to the present disclosure, which can simulate an operational environment of the flexible screen by moving the fixing device to conduct an extrusion test to the flexible screen, can reduce testing costs compared with the traditional methods and apparatuses for bending test of a flexible screen.

DETAILED DESCRIPTION OF THE PREFERRED EMBODIMENTS

In the following description of embodiments, reference is made to the accompanying drawings which form a part hereof, and in which it is shown by way of illustration specific embodiments of the disclosure that can be practiced. It is to be understood that other embodiments can be used and structural changes can be made without departing from the scope of the disclosed embodiments.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended, to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Figure 1:
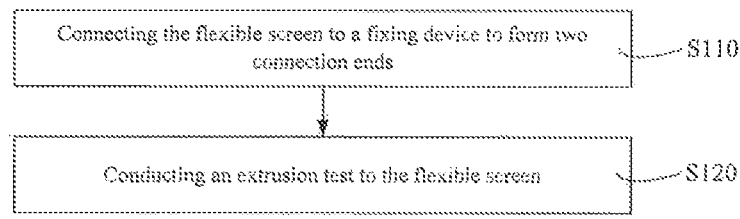
FIG. 1 is a flow diagram illustrating a method for bending test of a flexible screen according to one embodiment of the present disclosure.

As shown in FIG. 1, a method for bending, test of a flexible screen includes:

Step S110, connecting the flexible screen to a fixing device to form two connection ends.

The flexible screen can be connected with the fixing device in a point connection, a line connection or a face connection, and correspondingly, the two connection ends formed on the fixing device can be connection points, connection lines or connection faces.

In the embodiment, the two connection ends are located on opposite sides of the flexible screen respectively, and the connecting line between the two connection ends is perpendicular to a side edge of the flexible screen. In this way, it can ensure that portions of the flexible screen on both side of the connecting line between the two connection ends are uniformly forced when conducting an extrusion test to the flexible screen, to improve the efficiency of the extrusion test and avoid possible damage of the flexible screen caused by uneven force.

Step S120, conducting an extrusion test to the flexible screen, including moving the fixing device to change the distance between the connection ends of the fixing device so that the distance is less than or equal to the length of the flexible screen between the two connection ends. Conduct an extrusion test to the flexible screen, and simulate a practical application environment of the flexible screen.

In one embodiment, conducting an extrusion test to the flexible screen includes: extruding the flexible screen in a direction along a connecting line between the two connection ends; or moving the fixing device respectively along directions which are parallel to each other to extrude the flexible screen.

Extruding the flexible screen in a direction along a connecting line between the two connection ends can bend the flexible screen. As might be imagined, the flexible screen may be in a curve shape of "U" at this moment. Further, extruding the flexible screen in the direction along the connecting line between the two connection ends includes: moving the fixing device in a direction along the connecting line between the two connection ends for a predetermined magnitude, and extruding the flexible screen at a predetermined number of times, in which a plurality of predetermined magnitudes may be provided. That is, in the embodiment, the fixing device may be moved for a different predetermined magnitude to extrude the flexible screen, and it can better conform to the practical application environment of the flexible screen, and improve the accuracy of the test.

For moving the fixing device respectively along directions which are parallel to each other to extrude the flexible screen, the fixing device can be moved along parallel horizontal directions, vertical directions or other directions, to extrude the flexible screen to bend the flexible screen. When the direction of the extrusion is the same as the direction of the connection line between the two connection ends, the flexible screen may be in a curve shape of "U"; and when the direction of the extrusion is different from the direction of the connection line between the two connection ends, the flexible screen may be in a curve shape of "S". In the embodiment, the flexible screen may be extruded to be in a different curve shape, which can also improve the simulation of the practical application environment of the flexible screen and further improve the accuracy of the test.

In one embodiment, moving the fixing device respectively along directions which are parallel to each other to extrude the flexible screen includes: moving the fixing device respectively along a first plurality of directions which are parallel to each other to extrude the flexible screen, and moving the fixing device respectively along a second plurality of directions which are parallel to each other to extrude the flexible screen. In the embodiment, the first plurality of directions is perpendicular to the second plurality of directions, and in this way, it can simplify the operation and improve the efficiency when extruding the flexible screen. It can be appropriate that the first plurality of directions and the second plurality of directions are not determinate.

For example, both of the first plurality of directions and the second plurality of directions are not the same as the direction of the connection line between the two connection ends, and when the fixing device is moved in the first plurality of directions to extrude the flexible screen, the flexible screen may be in a curve shape of "S". The fixing device may be moved in the second plurality of directions to extrude the flexible screen when the flexible screen has been extruded in the first plurality of directions; or the fixing device may be moved in the second plurality of directions to extrude the flexible screen when the flexible screen has been restored to its initial state after being extruded in the first plurality of directions, in which the initial state is a state of the flexible screen before the extrusion test. If the former, the flexible screen is extruded in another direction when it is in a curve shape of "S", and the bending radius of the flexible screen is changed. If the latter, the flexible screen is extruded in another direction to be in a curve shape of "S" again after the flexible screen has been restored from being extruded to be in a curve shape of "S" to its initial state. In either case, the diversity of the extrusion ways of the flexible screen is increased, which can better conform to the practical application environment of the flexible screen, and improve the accuracy of the test.

Further, conducting an extrusion test to the flexible screen includes moving the fixing device in the first plurality of directions for a preset magnitude to extrude the flexible screen at a first preset number of times, and moving the fixing device in the second plurality of directions for a predetermined magnitude to extrude the flexible screen at a second preset number of times. The flexible screen can be extruded in the first plurality of directions and the second plurality of directions for a number of times, which can further conform to the practical application environment of the flexible screen.

Further, there is a plurality of preset magnitudes and/or a plurality of predetermined magnitudes. For example, there is a plurality of preset magnitudes and a plurality of predetermined magnitudes, the preset magnitudes includes a magnitude A, a magnitude B, a magnitude C, and the predetermined magnitudes includes a magnitude A', a magnitude B', a magnitude C'. If all of the preset magnitudes correspond to multiple predetermined magnitudes, the flexible screen may be extruded in the first plurality of directions for the magnitude A at the first preset number of times, and the flexible screen may be extruded in the second plurality of directions for at least two of the magnitude A', the magnitude B' and the magnitude C' respectively, at the second preset number of times. Similarly, after the flexible screen is extruded in the first plurality of directions for the magnitude B or C at the first preset number of times, the flexible screen may be extruded in the second plurality of directions for at least two of the magnitude A', the magnitude B' and the magnitude C' respectively. It can further conform to the practical application environment of the flexible screen that the flexible screen can be extruded for a different magnitude in the first plurality of directions and the second plurality of directions, which improves the accuracy of the test.

In one embodiment, conducting an extrusion test to the flexible screen includes moving the fixing device in the direction along the connecting line between the two connection ends for a predetermined magnitude to extrude the flexible screen at a predetermined number of times, to bend the flexible screen in a curve shape of "U"; moving the fixing device respectively in the first plurality of directions for a preset magnitude to extrude the flexible screen at the first preset number of times, to bend the flexible screen in a curve shape of "S"; and moving the fixing device in the second plurality of directions for a predetermined magnitude to extrude the flexible screen at the second preset number of times.

The above method for bending test of a flexible screen connect the flexible screen to a fixing device to form two connection ends, and conduct an extrusion test to the flexible screen, including moving the fixing device to change the distance between the connection ends of the fixing device so that the distance is less than or equal to the length of the flexible screen between the two connection ends. The above method, that simulates an operational environment of the flexible screen by moving the fixing device to conduct an extrusion test to the flexible screen, can reduce testing costs compared with the traditional methods and apparatuses for bending test of a flexible screen.

In one embodiment, after step S120, the method for bending test of a flexible screen further includes:

conducting a performance detection to the flexible screen.

Conducting a performance detection to the flexible screen includes: detecting the mechanical reliability of the flexible screen after conducting the extrusion test to the flexible screen.

The detecting the mechanical reliability of the flexible screen is detecting the extent of the damage at the flexible screen after the extrusion test. Specifically, the flexible screen may be scanned and detected by a scanner, and the flexible screen can be classified, for example, to good products, qualified products and defective products, according to the extent of the damage after getting the detection results. Then the flexible screen can be tagged with a level of its mechanical reliability.

Conducting a performance detection to the flexible screen further includes: detecting the optical reliability and/or electrical reliability of the flexible screen when conducting the extrusion test to the flexible screen or after conducting the extrusion test to the flexible screen.

For example, in one embodiment that the optical reliability and the electrical reliability are detected, the optical reliability is detected by detecting the light transmittance of the flexible screen by irradiating the flexible screen with a light source, and the electrical reliability is detected by detecting the electrical parameter of the semiconductor device in the flexible screen, specifically, including using a semiconductor parameter tester to connect the semiconductor device in the flexible screen, conducting an electrical parameter test, and evaluating the change of the electrical parameter before and after bending.

The performance detection to the flexible screen can be one or more of the detections of the mechanical reliability, the optical reliability and the electrical reliability of the flexible screen.

Figure 2A:
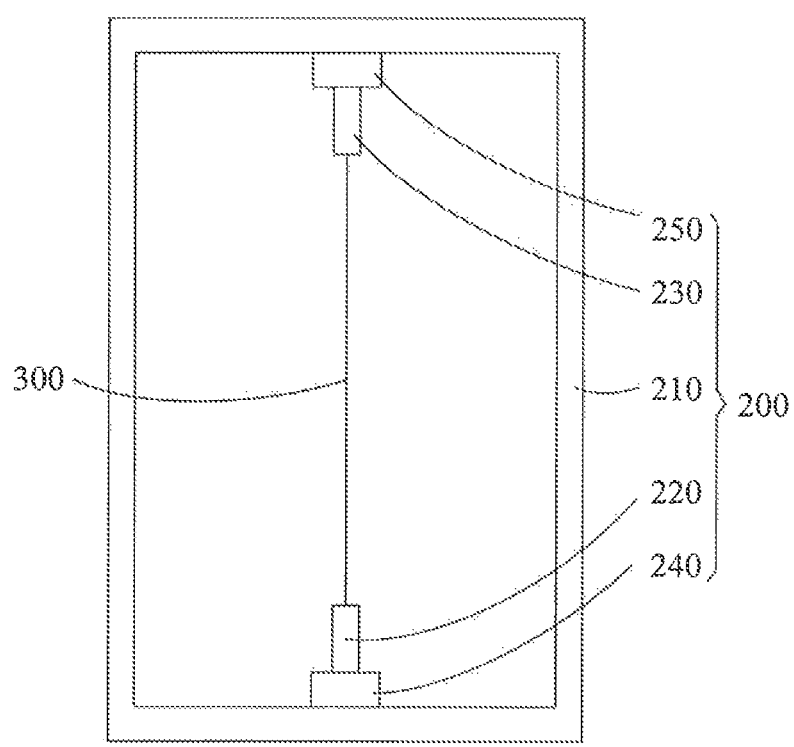
FIGS. 2A-2C are schematic diagrams illustrating of operations of a system for bending test of a flexible screen according to one embodiment of the present disclosure.

As shown in FIG. 2A, a system for bending test of a flexible screen is also provided, including a fixing device (not shown) and an extrusion device 200.

The fixing device is configured to be connected to the flexible screen 300 to form two connection ends.

The flexible screen can be connected with the fixing device 300 in a point connection, a line connection or a face connection, and correspondingly, the two connection ends formed on the fixing device can be connection points, connection lines or connection faces.

The fixing device includes a first clamp and a second clamp configured to be connected to opposing sides of the flexible screen 300 respectively to form two connection ends. In the embodiment, the connecting line between the two connection ends is perpendicular to a side edge of the flexible screen 300. In this way, it can ensure that portions of the flexible screen 300 on both side of the connecting line between the two connection ends are uniformly forced when conducting an extrusion test to the flexible screen, to improve the efficiency of the extrusion test and avoid possible damage of the flexible screen 300 caused by uneven force.

The extrusion device 200 is configured to move the fixing device to change the distance between the connection ends of the fixing device so that the distance is less than or equal to the length of the flexible screen 300 between the two connection ends, for conducting an extrusion test to the flexible screen 300, and simulating the practical application environment of the flexible screen.

In one embodiment, the extrusion device may includes a fixing support 210, a stretchable first tension rod 220 and a stretchable second tension rod 230 and a first base 240 and a second base 250.

One end of the first tension rod 220 and one end of the second tension rod 230 are connected to the first clamp and the second clamp respectively. The first clamp and the second clamp can be connected to the first tension rod 220 and the second tension rod 230 in a constant connection, such as welding or threaded connection. Alternatively, the first clamp and the second clamp can be connected to the first tension rod 220 and the second tension rod 230 in a movable connection, for example, by a rotatable connection device about a fixed axis. In the embodiment, the first clamp and the second clamp are movably connected with the first tension rod 220 and the second tension rod 230 respectively, so that the flexible screen 300 can swing freely. In this way, it can avoid the damage of the flexible screen 300 caused by an external force when conducting an extrusion test, to improve the accuracy of the test.

Each of the first base 240 and the second base 250 can be a base with a function of programmable drive motor, provided on the fixing support 210 and moveable relative to the fixing support 210.

In the embodiment, the fixing support 210 can be a hollow box or a similar mechanism. The first base 240 and the second base 250 are provided on the top and bottom of the interior of the fixing support 210 respectively. Specifically, the top and bottom of the interior of the fixing support 210 can be provided with a slidable guide rail respectively, and the first base 240 and the second base 250 can be moveable relative to the fixing support 210 via the slidable guide rails.

It will be appropriated that the concrete structures of the fixing support 210 and the positions of the first base 240 and the second base 250 provided on the fixing support 210 are not determinate.

The first base 240 and the second base 250 are connected to the other end of the first tension rod 220 and the other end of the second tension rod 230 respectively, and configured to control the length of each of the first tension rod 220 and the second tension rod 230 to be stretched, to extrude the flexible screen 300 in the direction along the connecting line between the two connection ends or move the fixing device respectively along directions which are parallel to each other to extrude the flexible screen 300.

Figure 2B:
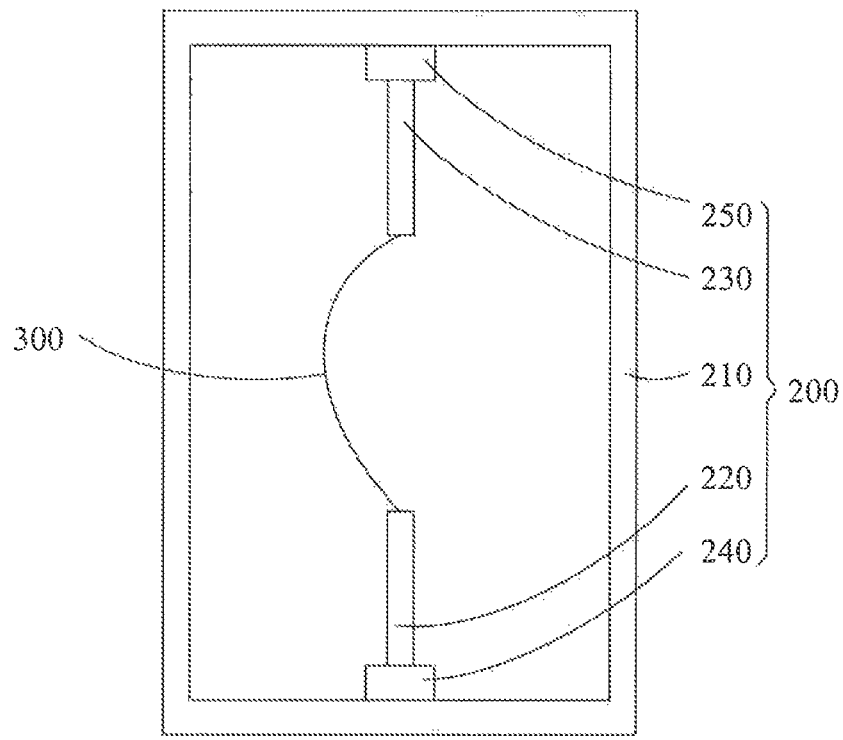
Figure 2C:
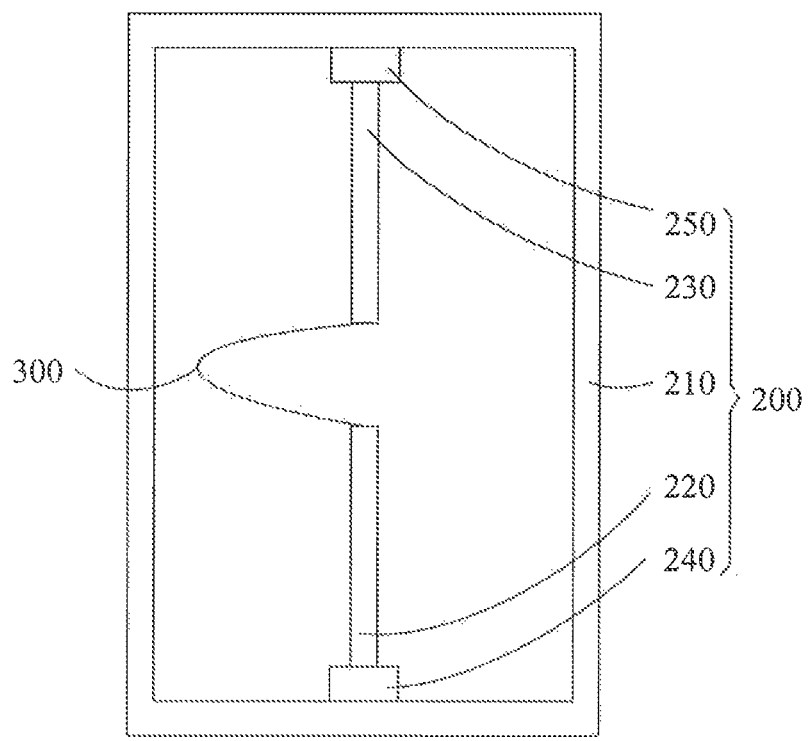

As shown in FIGS. 2A-2C, the flexible screen 300 can be extruded in a direction along a connecting line between the two connection ends and be bent to be in a curve shape of "U". In the embodiment, the connecting line between the two connection ends is in a vertical direction. Further, the first base 240 and the second base 250 can control the length of each of the first tension rod 220 and the second tension rod 230 to be stretched, to extrude the flexible screen in the direction along the connecting line between the two connection ends for a predetermined magnitude at a predetermined number of times, in which a plurality of predetermined magnitudes may be provided. The predetermined magnitude may be determined by the length of each of the first tension rod 220 and the second tension rod 230 to be stretched. In the embodiment, the flexible screen 300 can be extruded for a different predetermined magnitude, which can better conform to the practical application environment of the flexible screen 300, and improve the accuracy of the test.

The first base 240 and the second base 250 can control the length of each of the first tension rod 220 and the second tension rod 230 to be stretched, to move and extrude the flexible screen along directions which are parallel to each other. The fixing device can be moved along parallel horizontal directions, vertical directions or other directions, to extrude the flexible screen 300 to bend the flexible screen 300. When the direction of the extrusion is the same as the direction of the connection line between the two connection ends, the flexible screen 300 may be in a curve shape of "U"; and when the direction of the extrusion is different from the direction of the connection line between the two connection ends, the flexible screen 300 may be in a curve shape of "S". In the embodiment, the flexible screen 300 may be extruded to be in a different curve shape, which can also improve the simulation of the practical application environment of the flexible screen 300 and further improve the accuracy of the test.

In one embodiment, the first base 240 and the second base 250 can control the length of each of the first tension rod 220 and the second tension rod 230 to be stretched, to move and extrude the flexible screen 300 along a first plurality of directions which are parallel to each other, and the first base 240 and the second base 250 can move and extrude the flexible screen along a second plurality of directions which are parallel to each other. In the embodiment, the first plurality of directions is perpendicular to the second plurality of directions, and in this way, it can simplify the operation and improve the efficiency when extruding the flexible screen. It can be appropriate that the first plurality of directions and the second plurality of directions are not determinate.

Figure 3A:
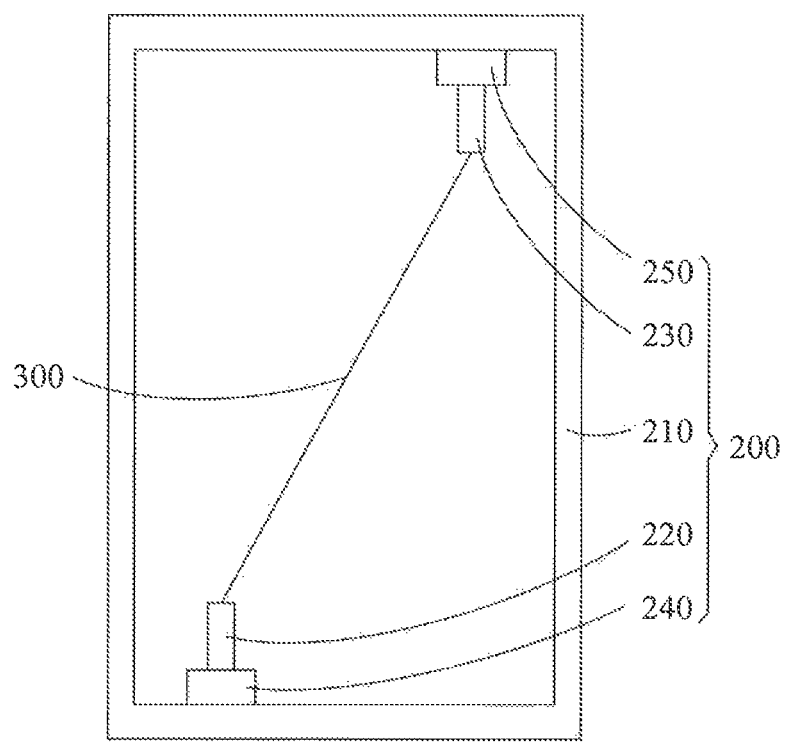
FIGS. 3A-3C are schematic diagrams illustrating of operations of a system for bending test of a flexible screen according to another embodiment of the present disclosure.
Figure 3B:
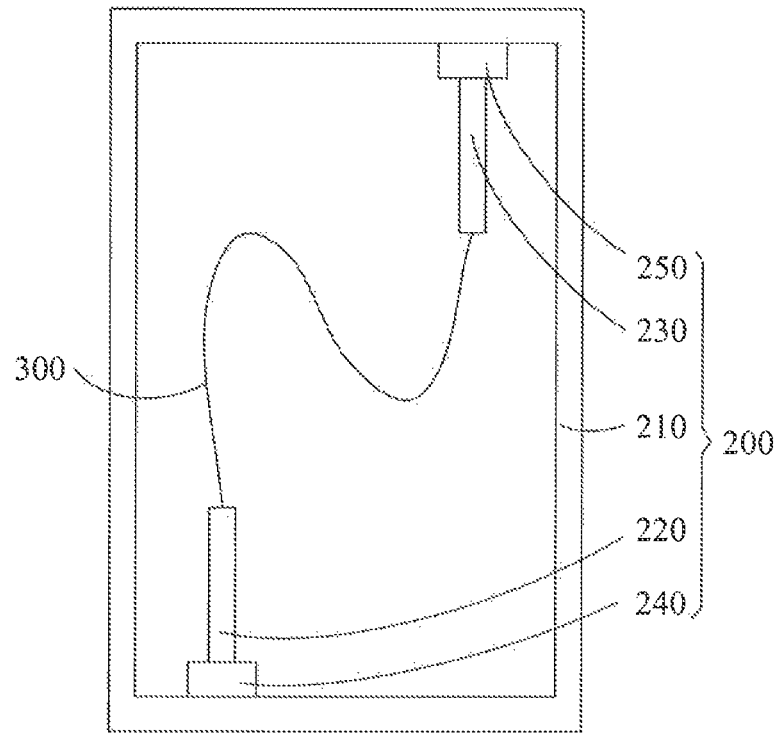
Figure 3C:
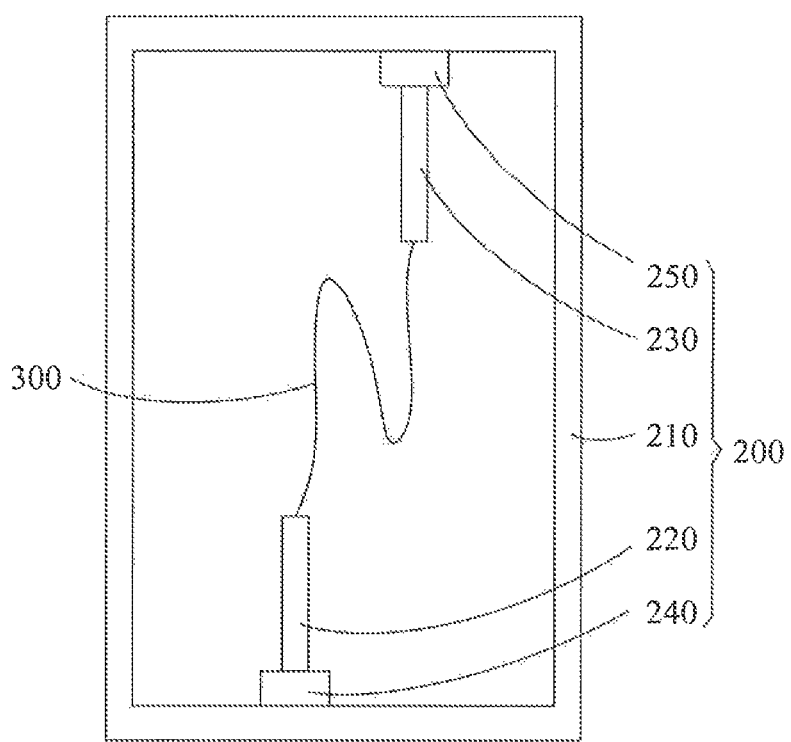

For example, both of the first plurality of directions and the second plurality of directions are not the same as the direction of the connection line between the two connection ends, the first plurality of directions are vertical, and the second plurality of directions are horizontal, as shown in FIGS. 3A-3C. When the first base 240 and the second base 250 can control the length of each of the first tension rod 220 and the second tension rod 230 to be stretched, to move and extrude the flexible screen 300 in the first plurality of directions, the flexible screen may be in a curve shape of "S". The first base 240 and the second base 250 can move relatively to the fixing support 210 to move and extrude the flexible screen 300 in the second plurality of directions when the flexible screen 300 has been extruded in the first plurality of directions; or the first base 240 and the second base 250 can move relatively to the fixing support 210 to move and extrude the flexible screen 300 in the second plurality of directions when the flexible screen 300 has been restored to its initial state after being extruded in the first plurality of directions, in which the initial state is a state of the flexible screen 300 before the extrusion test. If the former, the flexible screen 300 is extruded in another direction when it is in a curve shape of "S" and the bending radius of the flexible screen 300 is changed. If the latter, the flexible screen 300 is extruded in another direction to be in a curve shape of "S" again after the flexible screen 300 has been restored from being extruded to be in a curve shape of "S" to its initial state. In either case, the diversity of the extrusion ways of the flexible screen 300 is increased, which can better conform to the practical application environment of the flexible screen 300, and improve the accuracy of the test. FIGS. 3A-3C show the flexible screen 300 is extruded in the second plurality of directions, after it has been in a curve shape of "S" in the first plurality of directions.

Further, the first base 240 and the second base 250 can control the length of each of the first tension rod 220 and the second tension rod 230 to be stretched, to move and extrude the flexible screen 300 respectively along the parallel first plurality of directions at a first preset number of times, and the first base 240 and the second base 250 can move and extrude the flexible screen 300 respectively along the parallel second plurality of directions at a second preset number of times. The flexible screen 300 can be extruded in the first plurality of directions and the second plurality of directions for a number of times, which can further conform to the practical application environment of the flexible screen 300.

Further, there is a plurality of preset magnitudes and/or a plurality of predetermined magnitudes. For example, there is a plurality of preset magnitudes and a plurality of predetermined magnitudes, the preset magnitudes includes a magnitude A, a magnitude B, a magnitude C, and the predetermined magnitudes includes a magnitude E, a magnitude F, a magnitude G. If all of the preset magnitudes correspond to multiple predetermined magnitudes, the flexible screen 300 may be extruded in the first plurality of directions for the magnitude A at the first preset number of times, and the flexible screen 300 may be extruded in the second plurality of directions for at least two of the magnitude A', the magnitude B' and the magnitude C' respectively, at the second preset number of times. Similarly, after the flexible screen 300 is extruded in the first plurality of directions for the magnitude B or C at the first preset number of times, the flexible screen 300 may be extruded in the second plurality of directions for at least two of the magnitude A', the magnitude B' and the magnitude C' respectively.

The preset magnitude can be determined by the length of each of the first tension rod 220 and the second tension rod 230 to be stretched, and the predetermined magnitude can be determined by the displacement distance of the first base 240 and the second base 250. It will be appropriated that the preset magnitude, the predetermined magnitude, the first preset number of times and the second preset number of times can be adjusted according to the actual conditions. It can further conform to the practical application environment of the flexible screen that the flexible screen 300 can be extruded for a different magnitude in the first plurality of directions and the second plurality of directions, which improves the accuracy of the test.

In one embodiment, the first base 240 and the second base 250 can control the length of each of the first tension rod 220 and the second tension rod 230 to be stretched, to extrude the flexible screen 300 in the direction along the connecting line between the two connection ends for a predetermined magnitude at a predetermined number of times to bend the flexible screen in a curve shape of "U", to extrude the flexible screen 300 in the first plurality of directions for a preset magnitude at the first preset number of times to bend the flexible screen in a curve shape of "S", and to extrude the flexible screen 300 in the second plurality of directions for a predetermined magnitude at the second preset number of times.

The above system for bending test of a flexible screen connect the flexible screen 300 to a fixing device to form two connection ends, and uses an extrusion device 200 to move the fixing device to change the distance between the connection ends of the fixing device so that the distance is less than or equal to the length of the flexible screen 300 between the two connection ends for conducting an extrusion test to the flexible screen. The above system, that simulates an operational environment of the flexible screen 300 by moving the fixing device to conduct an extrusion test to the flexible screen 300, can reduce testing costs compared with the traditional methods and apparatuses for bending test of a flexible screen.

In one embodiment, the system for bending test of a flexible screen further includes a detection device configured to conduct a performance detection to the flexible screen 300.

The performance detection to the flexible screen 300 can be one or more of the detections of the mechanical reliability, the optical reliability and the electrical reliability of the flexible screen 300. For example, in one embodiment that the performance detection includes the mechanical reliability, the optical reliability and the electrical reliability, the detection devices can include a scanner, an optical detector and an electrical detector.

The scanner is configured to scan the flexible screen 300 and detect the extent of the damage at the flexible screen 300 after the mechanical extrusion test. The flexible screen 300 can be classified, for example, to good products, qualified products and defective products, according to the extent of the damage after getting the detection results. Then the flexible screen 300 can be tagged with a level of its mechanical reliability.

The optical detector is configured to conduct an optical reliability test and detect the light transmittance of the flexible screen 300 in the extrusion test or after the extrusion test. The optical detector may include a light source part and a detection part respectively arranged on two sides of the flexible screen 300. The light signal form the light source part can irradiate the flexible screen 300, and the detection part can receive the light that passes through the flexible screen 300 to detect the light transmittance of the flexible screen.

The electrical detector is configured to conduct an electrical reliability test and detect the electrical parameter of the semiconductor device in the flexible screen 300 in the extrusion test or after the extrusion test. The electrical detector can be a semiconductor parameter tester which can be connected to the semiconductor device in the flexible screen for the electrical parameter test to evaluate the change of the electrical parameter before and after bending.

The above are preferred embodiments of the invention described in detail, and should not be deemed as limitations to the scope of the present invention. It should be noted that variations and improvements will become apparent to those skilled in the art to which the present invention pertains without departing from its spirit and scope. Therefore, the scope of the present disclosure is defined by the appended claims.

The invention claimed is:

1. A method for bending test of a flexible screen, comprising:
    connecting the flexible screen to a fixing device to form two connection ends; and
    conducting an extrusion test to the flexible screen, including moving the fixing device to change a distance between the connection ends of the fixing device so that the distance is less than or equal to a length of the flexible screen between the two connection ends,
    wherein conducting an extrusion test to the flexible screen includes:
    moving a first end of the fixing device along a first plurality of directions which are parallel to each other to extrude the flexible screen; and
    moving a second end of the fixing device along a second plurality of directions which are parallel to each other to extrude the flexible screen, the first plurality of directions being perpendicular to the second plurality of directions.

2. The method of claim 1, wherein conducting an extrusion test to the flexible screen comprises moving the first end of the fixing device in the first plurality of directions for a preset magnitude to extrude the flexible screen for a first preset number of times, and moving the second end of the fixing device in the second plurality of directions for a predetermined magnitude to extrude the flexible screen for a second preset number of times.

3. The method of claim 2, wherein there is a plurality of preset magnitudes and/or a plurality of predetermined magnitudes.

4. A system for bending test of a flexible screen, comprising:
    a fixing device, configured to be connected to the flexible screen to form two connection ends, wherein the fixing device comprises a first clamp and a second clamp configured to be connected to opposing sides of the flexible screen respectively to form two connection ends; and
    an extrusion device, configured to move the fixing device to change a distance between the connection ends of the fixing device so that the distance is less than or equal to a length of the flexible screen between the two connection ends, and to conduct an extrusion test to the flexible screen,
    wherein the extrusion device comprises:
    a fixing support;
    a stretchable first tension rod and a stretchable second tension rod, one end of the first tension rod and one end of the second tension rod being connected to the first clamp and the second clamp respectively;
    a first base and a second base provided on the fixing support and configured to be moveable relative to the fixing support and connected to the other end of the first tension rod and the other end of the second tension rod respectively, for controlling the length of each of the first tension rod and the second tension rod to be stretched, so as to extrude the flexible screen in the direction along the connecting line between the two connection ends or move the fixing device respectively along directions which are parallel to each other to extrude the flexible screen.

5. The system of claim 4, wherein the first clamp and the second clamp are movably connected with the first tension rod and the second tension rod respectively.

* * * * *